(12) United States Patent
Jen

(10) Patent No.: US 7,231,806 B2
(45) Date of Patent: Jun. 19, 2007

(54) APPARATUS AND METHOD FOR RAPIDLY, ECO-FRIENDLY SAMPLE PREPARATION PRIOR TO CHROMATOGRAPHIC DETERMINATION OF CHEMICAL SUBSTANCES

(76) Inventor: Jen-Fon Jen, 13F, No. 612, Wucyuan S. Rd., South District, Taichung City (TW)

( * ) Notice: Subject to any disclaimer, the term of this patent is extended or adjusted under 35 U.S.C. 154(b) by 0 days.

(21) Appl. No.: 11/441,247

(22) Filed: May 26, 2006

(65) Prior Publication Data

US 2006/0213252 A1    Sep. 28, 2006

Related U.S. Application Data

(62) Division of application No. 11/013,397, filed on Dec. 17, 2004.

(51) Int. Cl.
*G01N 30/12* (2006.01)
(52) U.S. Cl. .................. 73/23.2; 73/41; 73/19.02
(58) Field of Classification Search .............. 73/23.2, 73/23.35, 23.41, 19.02; 436/177, 178; 210/774
See application file for complete search history.

(56) References Cited

U.S. PATENT DOCUMENTS

| | | | | |
|---|---|---|---|---|
| 5,496,741 | A | * 3/1996 | Pawliszyn | .................... 436/163 |
| 5,998,217 | A | * 12/1999 | Rao et al. | .................... 436/179 |
| 2006/0019017 | A1 | * 1/2006 | Singh et al. | ................. 426/574 |
| 2006/0038118 | A1 | * 2/2006 | Collins et al. | .............. 250/251 |

* cited by examiner

*Primary Examiner*—Hezron Williams
*Assistant Examiner*—Ryan Christensen
(74) *Attorney, Agent, or Firm*—Birch, Stewart, Kolasch & Birch, LLP

(57) ABSTRACT

A method and apparatus for rapidly preprocessing and analyzing chemical substances, which places a vaporization bottle containing a sample inside a microwave device and uses a magneton driving device to drive the magneton inside the vaporization bottle to rotate as to stir the sample liquid even. In the meantime, the radiation of the electromagnetic wave of the microwave device is used to activate the molecules of the sample liquid to move, causing the tested chemical substance in the sample liquid to be vaporized in a very short time. Therefore, the tested chemical substance can be absorbed or adsorbed by the absorbing medium to greatly reduce the sample preprocessing time and increase the quantity of the tested chemical substance sample. The detection limits of a tested chemical substance are therefore lowered without using organic solvents.

7 Claims, 2 Drawing Sheets

APPARATUS AND METHOD FOR RAPIDLY, ECO-FRIENDLY SAMPLE PREPARATION PRIOR TO CHROMATOGRAPHIC DETERMINATION OF CHEMICAL SUBSTANCES

This application is a Divisional of co-pending application Ser. No. 11/013,397, filed on Dec. 17, 2004, and for which priority is claimed under 35 U.S.C. § 120, the entire contents of which are hereby incorporated by reference.

FIELD OF THE INVENTION

The present invention generally relates to a method and an apparatus for rapidly, eco-friendly sample preparation prior to chromatographic determination of chemical substances, more particularly to a method and an apparatus that can greatly shorten the preprocessing time for a sample and expedite the collecting process for semi-volatile, non-volatile, or low-volatile chemical substances from base bodies of samples, and to lower their detection limits.

BACKGROUND OF THE INVENTION

Traditional technologies including liquid-liquid extraction (LLE) or solid phase extraction (SPE) are generally used as the pretreatment process to clean up or pre-concentrate the target species prior to chromatographic analysis of organic substances. However, these methods have certain drawbacks such as complicated operation processes, time consumption, high cost, health damage due to the usage of organic solvents, and the high expense with respect to the disposal of toxic organic solvents. Therefore, U.S. company Supelco introduced a solid phase microextraction (SPME) technology to overcome part of the above mentioned shortcomings of the traditional technology for preprocessing samples, and such technology can directly extract volatile and non-volatile compounds in a liquid or gas without using solvents or complicated apparatus, and also can directly analyze the sample by a gas chromatograph (GC) or a high performance liquid chromatograph (HPLC) with specific detector, including manual and automatic models.

Later on, the immersing SPME method was found being significantly influenced by the complicated matrix of sample. To improve this shortcoming, the headspace method (HS) technology was used with SPME as the HS-SPME technology in the sample pretreatment process for complicated matrix samples prior to the analysis in past years. However, HS-SPME sampling is only suited for volatile analytes, or it will take a long time to finish the sampling of targeting analyzed species from base bodies of samples having moderate sensitivity and reproducibility. The headspace sampling technique is thus limited to semi-volatile organic compounds and analyzed species with high boiling points.

Recently, microwave-energy was widely applied in the sample pretreatment process prior to chemical analysis such as accelerating sample digestion and solvent extraction of target species from sample. Through the dipole rotation and ionic conductance of polar substances or ionic species under the microwave irradiation, the temperature of the system rises within a very short-time period. Therefore, microwave heating has the potential to improve the HS-SPME sampling for organic compounds.

SUMMARY OF THE INVENTION

The primary objective of the present invention is to overcome the foregoing shortcomings of the prior art by providing a way of shortening the sample preprocessing time for semi-volatile or low-volatile chemical analyte from base bodies of samples, so that the sample preprocessing can be completed within a few minutes.

Another objective of the present invention is to increase the quantity of analyte in the headspace sampling process as to the quantity of analyte injected into the chromatograph and thus lower the detection limits.

A further objective of the present invention is to preprocess a sample without using an organic solvent, not only lowering the operating cost, but also avoiding safety issues, health issues, and waste processing issues derived from using organic solvents.

The present invention installs a sample vaporization bottle in a microwave device to be connected to a temperature control device and a magneton is disposed in the vaporization bottle. A magneton driving device is used to drive the magneton inside the vaporization bottle to rotate. If the testing sample solution is placed inside the vaporization bottle, the magneton is rotated to stir the sample solution evenly for sample homogeneity, and the microwave radiation of the microwave device is used to rapidly heat and activate the molecules in sample solution. As a result, the testing chemical substance in sample solution can be vaporized into the sampling chamber in a very short time. The temperature of the sampling chamber can be controlled through a water circulation assembly. By controlling the temperature, the vaporized chemical substances with water are cooled and condensed to form a misty zone. The position of an absorbing (adsorbing) medium is placed on the low-end of the misty zone in the sampling chamber, and the testing chemical substance can be absorbed or adsorbed by the absorbing/adsorbing medium of the sample adsorbing device. After the microwave assisted HS-SPME sampling, the chemical substance absorbed or adsorbed on the absorbing or adsorbing medium are then analyzed by chromatography.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
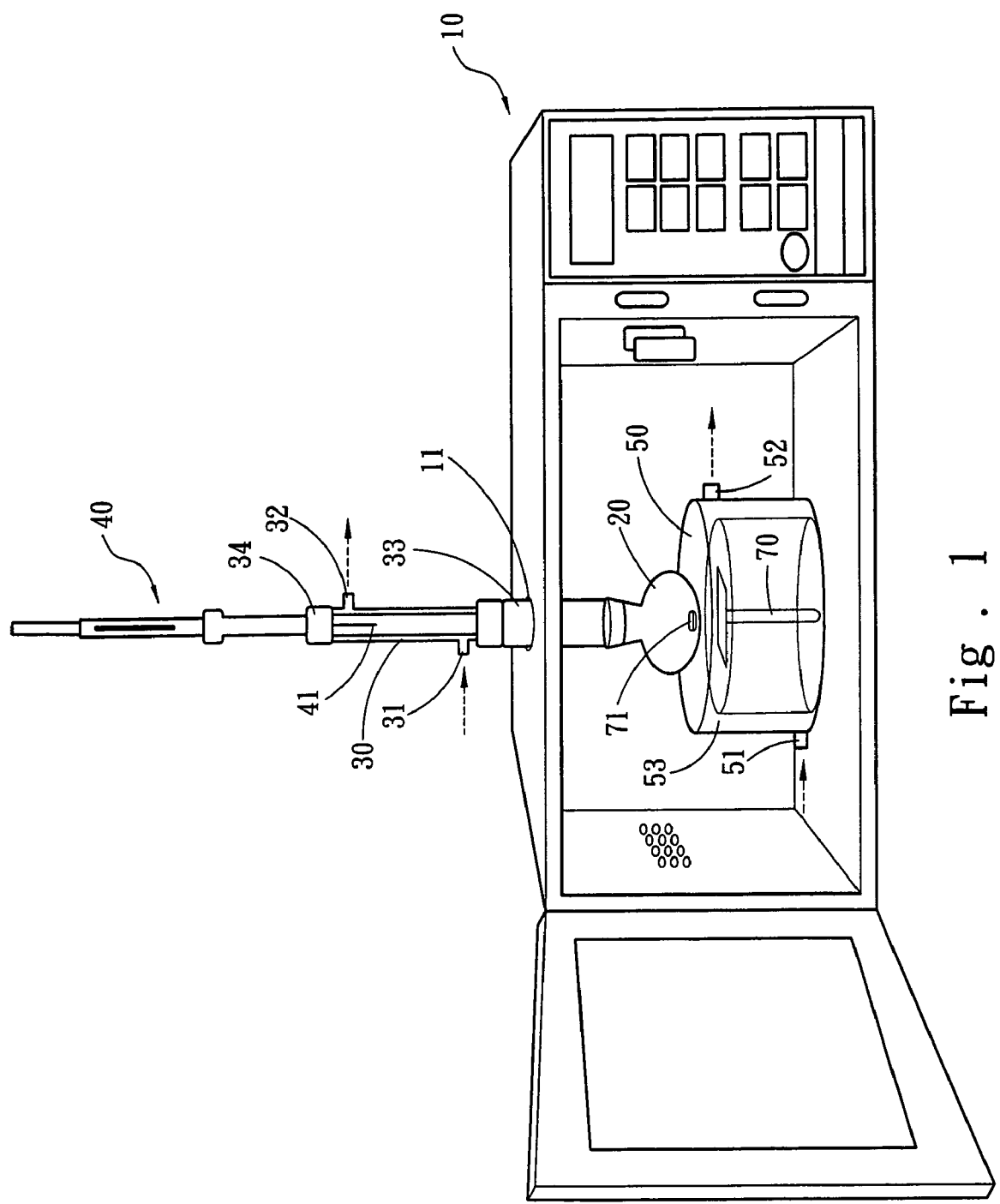
FIG. 1 is an illustrative view of the apparatus of the present invention.

Please refer to FIG. 1 for the view of the apparatus according to the present invention, which comprises a microwave device 10 such as a traditional microwave oven; a vaporization bottle 20 being disposed in the microwave device 10, and a magneton 71 being disposed in the vaporization bottle 20. A magneton driving device 70 is installed at the internal bottom surface of the microwave device 10 and disposed under the vaporization bottle 20, such that the magneton driving device 70 can drive the magneton 71 in the vaporization bottle 20 to rotate. If the testing chemical substance is placed in the vaporization bottle 20, the rotating magneton 71 can stir the testing chemical substance evenly.

The microwave device 10 further comprises a circulating water hood (a reverse U shape water jacket) 50 made of an organic or an inorganic material such as glass, plastic or ceramic, etc. The circulating water hood 50 is disposed between the vaporization bottle 20 and the magneton driving device 70, and covers the magneton driving device 70 to reduce the microwave power, so that the magneton driving device 70 will not be damaged by microwave radiations. The circulating water hood 50 comprises a water inlet 51, a water outlet 52, and a circulating space 53 filled with a protective water layer, and the thickness of the circulating space 53 is preferably at least 2 cm depending on the microwave properties.

A headspace temperature control sampling chamber 30 located in a cooling water jacket comprises a water inlet 31 and a water outlet 32 being externally connected to a water circulating machine (not shown in the figure) for temperature control, a connecting section 33 disposed at the bottom being connected to the mouth of the vaporization bottle 20 through a through-hole 11 at the top surface of the microwave device 10, and a fixed ring 34 disposed at the top; wherein the headspace temperature control sampling chamber 30 and the circulating water hood 50 can use the same circulating water system (not shown in the figure) to achieve the purpose of circulating water. Besides the water circulation method, the way of controlling the temperature of the headspace temperature control sampling chamber 30 could be a mechanical temperature control module, an electric temperature control module, and a thermoelectric cooling module.

A sample absorbing device 40 could be a solid phase microextraction (SPME) device, and one end of the sample absorbing device 40 has an absorbing medium 41, such that the sample absorbing device 40 can be fixed at the top of the headspace temperature control sampling chamber 30 by a fixed ring 34 and the absorbing medium 41 can be placed inside the headspace temperature control sampling chamber 30 with its height situated between the water inlet 31 and the water outlet 32 for absorbing or adsorbing the vaporized chemical substance by operating the apparatus of the present invention.

Further, the material of the absorbing medium 41 is selected according to the volatility and polarity of the analyte.

Figure 2:
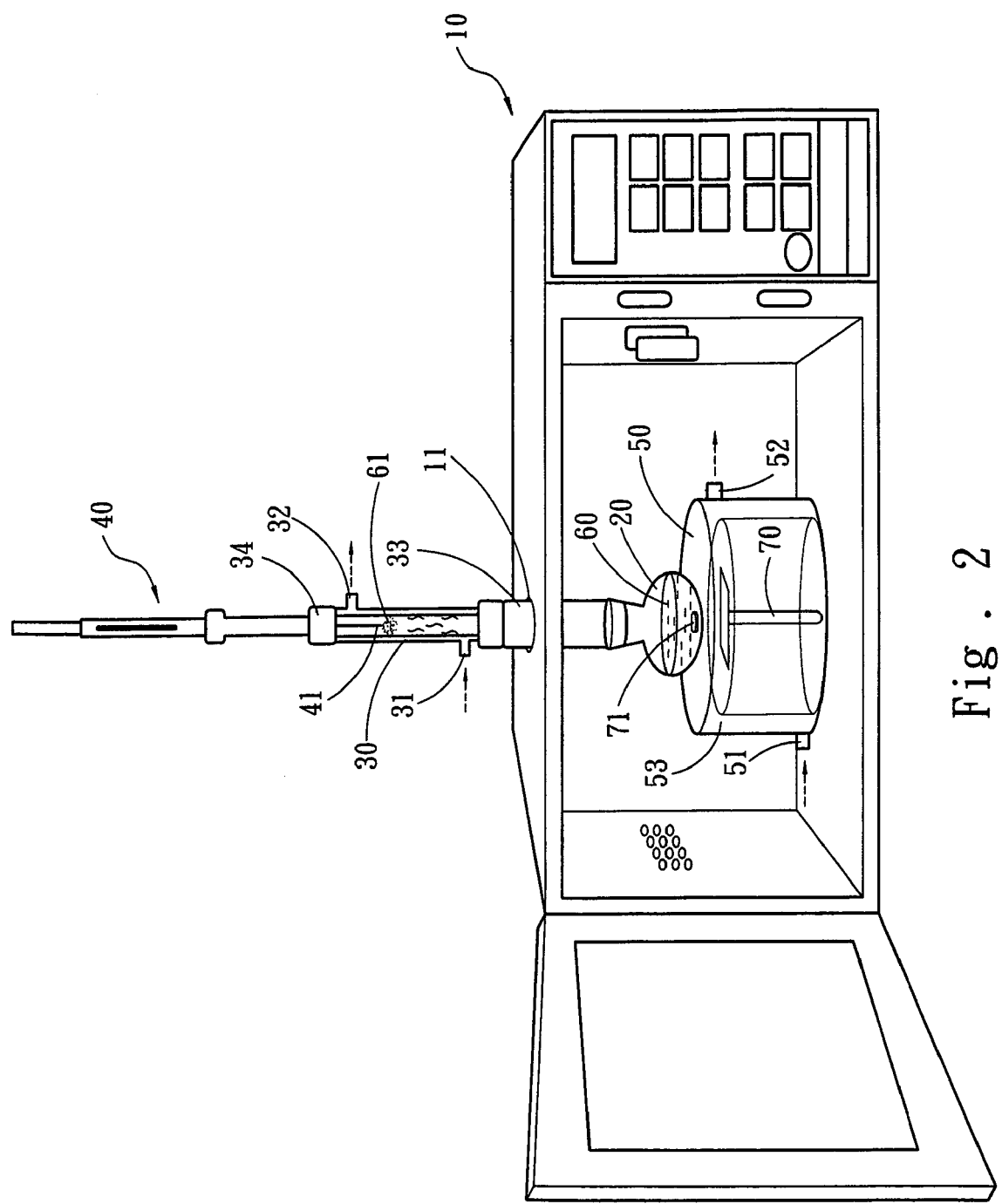
FIG. 2 is an illustrative view of the implementation of a preferred embodiment of the present invention.

Please refer to FIG. 2 for an illustrative view of the implementation of a preferred embodiment of the present invention. For the convenience of observing the internal structure of the invention better, the door of the microwave device 10 is opened as shown in the figure. The method for rapidly preprocessing chemical substances comprises the following steps:

(Step 1) Place a sample (a testing object in liquid or solid powder form) in a vaporization bottle 20, and add water to the sample to adjust its pH value and produce a sample liquid 60; wherein the pH value of the sample liquid 60 is adjusted according to the testing chemical substance.

(Step 2) A magneton driving device 70 drives a magneton 71 to rotate and stir the sample liquid 60 evenly as to rotate a magneton 71, while using the electromagnetic wave of a microwave device 10 to quickly heat the sample liquid 60 as to vaporize the testing chemical substance in the sample liquid 60 to the headspace temperature control sampling chamber 30. At this time, the headspace temperature control sampling chamber 30 is controlled through the circulated water. Due to such temperature control, the vaporized chemical substances and water are cooled to produce a misty zone 61. The position of the absorbing medium 41 in the headspace temperature control sampling chamber 30 during its operation is determined by the conversion of the testing chemical substances from gas state into a mist 61 of liquid state, so that the testing chemical substances can be absorbed or adsorbed by the absorbing medium 41 of the sample absorbing device 40.

The microwave irradiation power is adjusted according to the properties of the testing chemical substances. For example, the microwave irradiation power of the chlorophenols in a water sample (soil) under the best research parameter is 132W, and the sample collection time of the absorbing medium 41 is about 5 minutes. Under the irradiation power 145W for the polycyclic aromatic hydrocarbons (PAHs) in a water sample, the sample collection time of the absorbing medium 41 is about 30 minutes.

(Step 3) Inject the testing chemical substances absorbed and/or adsorbed in the absorbing medium 41 into gas chromatograph (GC) with various detectors to achieve the separation and detection.

The present invention uses a conventional microwave device 10 with wavelength of about 122 mm corresponding to the electromagnetic wave with a frequency of 2450 MHz. The molecules in the sample solution 60 oscillate with the same frequency of microwave to vigorously activate the movement, high-speed rotation, collision and friction among the molecules in the sample solution 60 and thus produce heat rapidly. Such arrangement can vaporize the testing chemical substances in a very short time (such as in a few minutes), and the expedited vaporization process accompanied with the controlled temperature to achieve the misty zone formation also speeds up the quantity of analyte to be absorbed or adsorbed onto the absorbing medium 41 and gives a sufficient testing quantity for chromatographic analysis. The on-line process makes its operation simpler and easier.

The rapid heating by microwave irradiation speeds up the vaporization of the semi-volatile, non-volatile or low volatile analyte, and thus shortens the sampling time. The vaporized species are condensed in misty zone and thus collected onto the absorbing or adsorbing medium 41. It increases the quantity of analytes absorbed or adsorbed on the absorbing or adsorbing medium 41, and thus increases the quantity of analytes injected into the chromatographic system which lowers the detection limits of analytes.

In the meantime, the sample preparation according to the present invention does not require any organic solvent, and thus not only lowering the cost, but also avoiding safety issues, health issues, and waste handling issues derived from using organic solvents.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An apparatus for rapidly preprocessing and thus analyzing chemical substances, comprising:
   a microwave device;
   a vaporization bottle disposed inside said microwave device, said vaporization bottle having a magneton inside;
   a magneton driving device disposed at the internal bottom surface of said microwave device and under said vaporization bottle for driving said magneton to rotate;

a headspace temperature control sampling chamber, having a concentric water-flow jacket with a water inlet and a water outlet for temperature control, a connecting section at the bottom being connected to the mouth of said vaporization bottle through a through hole at the top surface of said microwave device, and a fixed ring at the top; and a sample absorbing/adsorbing device fixed to the top of said headspace temperature control sampling chamber by said fixed ring, for selectively absorbing and adsorbing a vaporized chemical substance cooled in an internal tube of said headspace temperature control sampling chamber.

2. An apparatus for rapidly preprocessing and analyzing chemical substances, comprising:

a microwave device;

a vaporization bottle disposed inside said microwave device, said vaporization bottle having a magneton inside;

a magneton driving device disposed at the internal bottom surface of said microwave device and under said vaporization bottle for driving said magneton to rotate;

a headspace temperature control sampling chamber, having a concentric water-flow jacket with a water inlet and a water outlet for temperature control, a connecting section at the bottom being connected to the mouth of said vaporization bottle through a through hole at the top surface of said microwave device, and a fixed ring at the top; and a sample absorbing/adsorbing device fixed to the top of said headspace temperature control sampling chamber by said fixed ring, for selectively absorbing and adsorbing a vaporized chemical substance cooled in an internal tube of said headspace temperature control sampling chamber;

wherein said microwave device further comprises a circulating water hood therein, said circulating water hood being disposed between said vaporization bottle and said magneton driving device for covering said magneton driving device.

3. The apparatus for rapidly preprocessing and analyzing chemical substances of claim 2, wherein said circulating water hood comprises a water inlet, a water outlet, and a circulating space filled with a protective water layer and disposed between the internal wall and the external wall of said circulating water hood.

4. The apparatus for rapidly preprocessing and analyzing chemical substances of claim 2, wherein said circulating water hood is made of a material selected from the collection of glass, plastic, ceramic, organic and inorganic materials.

5. The apparatus for rapidly preprocessing and analyzing chemical substances of claim 1, wherein said headspace temperature control sampling chamber adopts a temperature control selected from the collection of a mechanical temperature control module, an electric temperature control module, and a thermoelectric cooling module.

6. The apparatus for rapidly preprocessing and analyzing chemical substance of claim 1, wherein said sample absorbing device is selected from a solid phase microextraction (SPME) device and liquid phase microextraction device.

7. An apparatus for rapidly preprocessing and analyzing chemical substances, comprising;

a microwave device;

a vaporization bottle disposed inside said microwave device, said vaporization bottle having a magneton inside;

a magneton driving device disposed at the internal bottom surface of said microwave device and under said vaporization bottle for driving said magneton to rotate;

a headspace temperature control sampling chamber, having a concentric water-flow jacket with a water inlet and a water outlet for temperature control, a connecting section at the bottom being connected to the mouth of said vaporization bottle through a through hole at the top surface of said microwave device, and a fixed ring at the top; and a sample absorbing/adsorbing device fixed to the top of said headspace temperature control sampling chamber by said fixed ring, for selectively absorbing and adsorbing a vaporized chemical substance cooled in an internal tube of said headspace temperature control sampling chamber;

wherein one end of the sample absorbing/adsorbing device comprises an absorbing medium in an internal tube of said headspace temperature control sampling chamber for controlling temperature and cooling, at a height situated between said water inlet and said water outlet.

* * * * *